United States Patent [19]

Perri et al.

[11] Patent Number: 4,530,902

[45] Date of Patent: Jul. 23, 1985

[54] METHOD FOR PRODUCING FRUCTOSE-1,6-DIPHOSPHORIC ACID

[75] Inventors: Giulio C. Perri, Milan; Tommaso Bianco, Pomezia; Beniamino Piccirilli, Belluno, all of Italy

[73] Assignee: Biomedica Foscama Industria Chimico Farmaceutica S.p.A., Rome, Italy

[21] Appl. No.: 80,016

[22] Filed: Sep. 28, 1979

[30] Foreign Application Priority Data

Jan. 16, 1979 [IT] Italy ............................... 47658 A/79

[51] Int. Cl.$^3$ ............................................. C07H 11/04
[52] U.S. Cl. .................................. 435/105; 536/117; 435/137; 435/276
[58] Field of Search ................ 536/117; 435/105, 137, 435/276

[56] References Cited

U.S. PATENT DOCUMENTS 3,379,168  3/1968  Curtin et al. ........................ 536/117
3,408,257  10/1968  Kauamori et al. .................. 536/117
3,469,989  9/1969  Gagolski et al. .................... 536/117

OTHER PUBLICATIONS

"Fructose-1,6-Diphosphoric Acid and Fructose-6-Monophosphoric Acid", C. Newberg et al., New York, (1943), pp. 33–43.

*Primary Examiner*—John F. Niebling
*Attorney, Agent, or Firm*—Michael J. Striker

[57] ABSTRACT

A ferric salt of the fructose-1,6-diphosphate is disclosed, which can be precipitated quantitatively from FDP-containing mixtures and has the formula $(FDP)_3Fe_4$. For preparing such salt, a ferric salt and an alkali are added to a fermentation broth which contains FDP, whereafter the precipitate is thoroughly water washed to remove the alkali metal salt and the washed solids are dried or frozen. The ferric salt has many advantages over the calcium salt used heretofore and no organic solvents are any more required.

4 Claims, No Drawings

METHOD FOR PRODUCING FRUCTOSE-1,6-DIPHOSPHORIC ACID

This invention relates to the ferric salt of fructose-1,6-diphosphate, a process for its preparation and for its use in the preparation of the fructose-1,6-diphosphoric acid. More particularly, the invention relates to a novel compound which can chemically be defined as the ferric salt of fructose-1,6-diphosphate, $(FDP)_3Fe_4$ which is a useful intermediate for the preparation of substances having a pharmacological activity, such as the already cited fructose-1,6-diphosphoric acid and the method for preparing the latter acid.

As compared with the known salts of fructose-1,6-diphosphate (FDP) and more particularly of the alkaline-earth metal salts thereof such as the calcium salt, the ferric salt $(FDP)_3Fe_4$, the subject matter of this invention, not described by the scientific literature, differs for its property of being precipitated as a pure salt under such pH conditions as to make it possible that the major fraction of the impurities remain in solution.

As it is apparent, such a property of $(FDP)_3Fe_4$ makes is possible to separate such a salt from any mixture wich contains FDP together with phosphates, monophosphorylated sugars, aminoacids, purines, pyrimidines etc., such as for example from fermentation broths, with virtually quantitative yields, a high purity and a molar stoichiometric ratio of 3 mols of FDP per 4 mols of iron.

As a matter of fact, as has suprisingly been found, the precipitation of the ferric salt takes place quantitatively for very low pH values (pH 1.2 to 4), whereas for the alkaline earth metal salts and more particularly for the calcium salt mentioned above, this is possible on an industrial scale for much higher values of the pH only, for example, for the calcium salt at pH 8 to 8.3. The result is that the calcium salt is precipitated from the fermentation broths together with the major fraction of the impurities which are insoluble for values of the pH in the range cited above (8 to 8.3).

The subsequent separation of the calcium salt from the impurities by washing with water is especially cumbersome due to the high water solubility of this salt.

This circumstance has suggested to the prior art the necessity of employing, both in the precipitation stage and in the washing stage, an organic solvent, such as acetone, which is capable of lowering the solbulity of the calcium salt relative to that of the impurities to obtain a production of salt under commercially and economically acceptable terms. However, due to the still fair solubility of the salt, this procedure does not make possible that thorough washing which would be necessary to obtain a high-purity product.

Therefore, the product of this invention $(FDP)_3Fe_4$ affords, as compared with the calcium salt and the other alkaline earth metals of the prior art, the advantage of a higher purity.

Another advantage of the invention is that the properties of the iron salt make possible an improved yield in the precipitation stage along with a lesser product loss in the washing stage.

Moreover, the precipitation and washing procedures are simplified inasmuch as there is no necessity of additionally employing those organic solvents, such as acetone, which are necessary in the case of alkaline earth salts so as to reduce the prime costs and the risks due to the toxicity of said solvents.

After all the control and the automation of the process for the production of the iron salt are strongly facilitated.

Lastly the use of the iron salt instead of the calcium salt in the preparation of the fructose-1,6-diphosphoric acid, which is a product well known in pharmacology particularly as metabolic regulator of the cardiac and postoperative reanimation, simplifies the productive procedure.

In fact the steps of repeated washing and dissolving in oxalic acid can be removed which were absolutely necessaries because of the presence of impurities in the calcium salt. On this subject it is very important that, because of the high toxicity, the use of the oxalic acid is eliminated.

Thus on industrial product is obtained which has a higher chemical purity. The yield is greatly improved and so the costs are further reduced.

Therefore the specific object of this invention is an iron salt of the fructose-1,6-diphosphate of formula $(FDP)_3Fe_4$ characterized by the fact that it can be quantitatively precipitated from mixtures containing FDP at a pH comprised between 1.2 and 4.

The invention relates also to a method for the production of that salt, which method is characterized by the operations of precipitating the ferric salt of the fructose-1,6-diphosphate from fermentation broths which contain FDP, by addition of a stoichiometric amount of a ferric salt and of an alkali to adjust the pH between 1.8 and 2, washing the thus obtained precipitate with water until the as-formed alkali metal salt is discharged and drying (or freezing) the product obtained in a form which is suitable for storage.

In a preferred embodiment of the invention, the ferric salt which is used is ferric chloride, the alkali is sodium hydroxide and the process is conducted at a pH of 2 then repeatedly washing the precipitate until the chlorides have been discharged.

A product is obtained, $(FDP)_3Fe_4$ which is extremely pure and is particularly suitable for being used in the pharmaceutical field, such as for the production of the fructose-1,6-diphosphoric acid.

As is well know, this latter acid is obtained, at present, starting from the calcium salt $(FDP)Ca_2$ of the fructose-1,6-diphosphate, the production of which is not only more intricate than that of the iron salt of this invention, but gives a product having a poorer purity.

As will be set forth more particularly in the ensuing examples which are reported by way of illustration and without limitation, it will be possible to appreciate, in the technical procedure for preparing the iron salt, the elimination of the use of organic solvents, such as acetone, which were necessary to decrease the too high solubility of the calcium salt, so that commercially acceptable separation and purification are made possible.

EXAMPLE I

Preparation of the calcium salt $(FDP)Ca_2$

To 500 liters of a fermentation broth having a concentration of $FDPH_4$ of 46.5 grams/liter, 45 kilograms of $CaCl_2.6H_2O$ are added.

The pH is adjusted to nearly 8 with 30% aqueous NaOH 30 liters of acetone are added. The precipitate thus obtained, stripped of its mother liquor by filtration, is washed batchwise with 100 liters of $H_2O$ and 5 liters of acetone.

After pressing and granulation the solid is dried in a fluid bed. Granulation is repeated and vacuum drying is applied.

There are obtained 31.6 kg of 63% pure calcium salt with a yield of 70%, corresponding to 16.27 kg of $FDPH_4$.

EXAMPLE II

Production of the iron salt $(FDP)_3Fe_4$

To 500 liters of a fermentation broth having a concentration of $FDPH_4$ of 46.5 grams/liter, 50 liters of a 50% solution of $FeCl_3.6H_2O$ are added with stirring. The pH is adjusted to nearly 2 with 25% NaOH.

The as-formed precipitate is separated by filtration from its mother liquors and washed three times with 1,000 liters of $H_2O$ each time. After pressing and granulation, the solid is dried on a fluid bed drier. Granulation is repeated and vacuum drying is applied.

There are obtained in this manner 33.8 kg of 80% pure iron salt, with a yield of 96.3%, corresponding to 22.39 kg of $FDPH_4$.

The ferric salt thus obtained is a powder which is virtually insoluble in $H_2O$, its solubility being 0.23 milligrams per milliliter at 20° C., and 0.40 mg/ml at 40' C.

Conversely, the salt is soluble in 10% NaOH, in $NH_4OH$ and in strong mineral acids.

The IR spectrum confirms the characteristics of sugar with peaks at 3400 $cm^{-1}$, 1650 $cm^{-1}$, 1090 $cm^{-1}$ and 1010 $cm^{-1}$.

Thin-layer chromatography on cellulose sheets (isobutyric acid, $H_2O$, $NH_4OH$ 66/33/1 as dyed solvent system with ammonium molybdate 12.5%, conc.HCl 8/3, perchloric acid (12 normal) 3 parts and acetone 86 parts), gives a spot of FDP Rf.0.13 and a very small amount of $PO_4^{--}$ at Rf.0.30.

The microanalysis on a sample indicates a formula $(FDPH_3)_4Fe_4$ corresponding to a mol wt of 1231.73.

| Composition, % by wt | Calculated | Found |
|---|---|---|
| C | 14.71 | 14.51 |
| H | 4.21 | 3.79 |
| Fe | 11.68 | 11.56 |
| $H_2O$ | — | 14.22 |

Enzymic activity of the powder: 55.48%

The following Table reports the percentage compositions of a few lots of iron salts and of calcium salts.

| PERCENTAGE COMPOSITION OF A FEW LOTS OF IRON SALT IN COMPARISON WITH LOTS OF CALCIUM SALT | | | | | | |
|---|---|---|---|---|---|---|
| | Iron salt | | | Calcium salt | | |
| Lots | Ca 12-055 | CA 12-060* | BM-0016 | BM-0023* | BM-0020* | CA 12-061* |
| Components | | | | | | |
| $FDPCa_2$ enz. | | | | | 71.7 | 70.5 |
| Iron salt $3FDPH_4 + 4Fe$ | 80.7 | 80.5 | 76.8 | 80.2 | | |
| Moisture, K.F. | 15.4 | 12.5 | 18.8 | 10.2 | 9.5 | 15.6 |
| Phosphorus, as $PO_4^{--}$ | 1.2 | 0.8 | 1.0** | 1.0 | 3.8 | 3.2 |
| Excess of Fe, as $Fe^{++}$ | 0.3 | 0.4 | 0.6 | 0.6 | | |
| Excess of Ca, as $Ca^{++}$ | | | | | 4.6 | 4.7 |
| Nitrogen, as Nx6.25 | 0.9 | 1.0 | 1.46 | 1.0** | 0.3 | 3.1 |
| Total monophosphates | 98.5 | 95.2 | 98.7 | 93.0 | 89.9 | 97.2 |
| % recovery of $FDPH_4$ | 92.0 | 91.0 | 92.2 | 87.8 | 21.3 | 30 |
| THIN-LAYER CHROMATOGRAPHY | | | | | | |
| Phosphates Rf. = 0.30 | traces | traces | — | traces | Mp | Mp |
| F6P and F1P Rf. = 0.22 | traces | traces | — | traces | Mp | Mp |
| F6P Rf. = 0.19 | min. | min. | — | min. | | |
| FDP Rf. = 0.13 | MG | MG | — | MG | MG | MG |

*Preparations referred to the tests in parallel
**Results obtained from the average of other lots.

From the results of the analyses it can be seen that:

(a) The iron salt is enzymically purer than the calcium salt.

(b) The iron salt is much purer chromatographically: the thin layer shows amounts of monophosphorylated sugars, of inorganic phosphorus and other impurities, which are much lower than those present in the calcium salt.

(c) In the iron salt the content of inorganic phosphorus is extremely low relative to the calcium salt.

(d) The recovery obtained in the preparations of the iron salt calculated on the basis of the content of $FDPH_4$, is definitely higher than the recoveries which are obtained usually for the calcium salt (recoveries of iron salt about 90%; recoveries of calcium salt about 55% after washing).

The ferric salt obtained according to the present invention is used, as aforesaid, for the production of the fructose-1,6-diphosphoric acid with a considerable advantage, due to its higher purity, the elimination of the purification steps which were necessary, conversely when using as the starting material the calcium salt which is less pure.

More precisely, the calcium salt as adopted at present must be subjected, prior to being treated in a cationic exchange column, to a prolonged series of a number of washings and then to the treatment with oxalic acid which is an efficient precipitation agent but is highly toxic. Working at a pH of about 1.9 which corresponds to the maximum amount of oxalic acid which can be accepted in the industry for safety reasons, the calcium salt precipitates as oxalate and the monocalcium salt of the fructose-1,6-diphosphate passes into solution whereafter the column treatment is performed.

As will become more clearly apparent from the ensuing examples, these two operational steps are dispensed with and the starting material is the ferric salt according to the invention and, moreover, an end product of higher purity, $(FDPH_4)$ will be obtained.

EXAMPLE III

Production of $FDPH_4$ from $(FDP)Ca_2$ 31.6 kg of fructose-1,6-diphosphate, calcium salt, are repeatedly washed, each time with 70 liters of $H_2O$ batchwise.

Oxalic acid is added to a pH or 1.9.

The slurry is filtered and the filtrate is decolorized with activated charcoal and treated with 70 liters of a strong cationic resin. There are obtained 120 liters of a 10% solution of $FDPH_4$, the yield being 74%.

EXAMPLE IV

Production of $FDPH_4$ from $(FDP)_3Fe_4$ 31.6 kg of fructose-1,6-diphosphate, iron salt, are treated batchwise with 300 liters of a strong cationic resin until complete dissolution is achieved.

Column elution is then performed with the aid of a tail column (250 liters of resin) to retain the last traces of iron.

Upon decoloration with activated charcoal, there are obtained 530 liters of a 4% solution of $FDPH_4$. Yield 91.2%.

The present invention has been described with particular reference to a few specific embodiments, it being understood, however, that modifications and changes can be introduced therein without thereby departing from the scope of this invention.

Having thus described the present invention, what is claimed is:

1. A process for the production of an iron salt of the fructose-1,6-diphosphate having the formula $(FDP)_3Fe_4$ comprising the steps of:
   (a) adding to a fermentation broth which contains FDP a ferric salt in a stoichiometrical amount and an alkali until attaining a pH comprised within the range 1.8–2;
   (b) washing the precipitate obtained from (a) with water until the alkali metal salt is discharged, and
   (c) either drying or freezing.

2. The process of claim 1 wherein the ferric salt is ferric chloride and the alkali is sodium hydroxide or a hydroxide wherein the cation is selected from the group consisting essentially of potassium, calcium or lithium.

3. Process according to claim 2, characterized in that the pH of the fermentation broth is adjusted to the value of 2.

4. Process according to claim 1, characterized in that the precipitate, after repeated washings, is pressed in a press, granulated, dried in fluid bed dryers, granulated once again and vacuum dried.

* * * * *